(12) United States Patent
Soykan et al.

(10) Patent No.: US 7,155,288 B2
(45) Date of Patent: *Dec. 26, 2006

(54) METHOD AND SYSTEM FOR MYOCARDIAL INFARCTION REPAIR

(75) Inventors: Orhan Soykan, Shoreview, MN (US); Maura G. Donovan, St. Paul, MN (US)

(73) Assignee: Medtronic, Inc, Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/300,176

(22) Filed: Dec. 14, 2005

(65) Prior Publication Data

US 2006/0095089 A1    May 4, 2006

Related U.S. Application Data

(63) Continuation of application No. 10/692,878, filed on Oct. 24, 2003, now Pat. No. 7,031,775, which is a continuation of application No. 09/706,531, filed on Nov. 3, 2000, now Pat. No. 6,671,558, which is a continuation-in-part of application No. 09/654,185, filed on Sep. 1, 2000, now Pat. No. 6,775,574, which is a continuation of application No. 09/145,743, filed on Sep. 2, 1998, now Pat. No. 6,151,525.

(60) Provisional application No. 60/064,703, filed on Nov. 7, 1997.

(51) Int. Cl.
*A61N 1/08* (2006.01)
*A61N 63/00* (2006.01)
*A61N 1/18* (2006.01)

(52) U.S. Cl. ............... 607/50; 607/3; 600/16; 424/93.1

(58) Field of Classification Search .............. 607/3, 607/10, 17, 50; 600/12–15, 17, 36; 424/93.1
See application file for complete search history.

(56) References Cited

U.S. PATENT DOCUMENTS

| 4,256,115 A | 3/1981 | Bilitch ............... 128/419 |
| 4,379,459 A | 4/1983 | Stein ............. 128/419 PG |
| 4,411,268 A | 10/1983 | Cox ................. 128/421 |
| 4,476,868 A | 10/1984 | Thompson ........ 128/419 PG |
| 4,556,063 A | 12/1985 | Thompson et al. ... 128/419 PT |
| 4,791,911 A | 12/1988 | Magovern ............. 600/36 |
| 4,821,723 A | 4/1989 | Baker et al. ....... 128/419 D |
| 5,030,204 A | 7/1991 | Badger et al. ......... 604/95 |
| 5,060,660 A | 10/1991 | Gambale et al. ..... 128/772 |
| 5,069,680 A | 12/1991 | Grandjean ............ 623/3 |
| 5,104,393 A | 4/1992 | Isner et al. ........... 606/15 |
| 5,131,388 A | 7/1992 | Pless .............. 128/419 D |
| 5,144,949 A | 9/1992 | Olson ............. 128/419 PG |

(Continued)

FOREIGN PATENT DOCUMENTS

EP    0 487429 A1    5/1992

(Continued)

OTHER PUBLICATIONS

Acsadi, et al., Direct Gene Transfer and Expression into Rat Heart In-Vivo, The New Biologist, 3(1):71-81, 1991.

(Continued)

*Primary Examiner*—Willis R. Wolfe, Jr.
(74) *Attorney, Agent, or Firm*—Kenneth J Collier

(57) ABSTRACT

An implantable system is provided that includes: a cell repopulation source comprising genetic material, undifferentiated and/or differentiated contractile cells, or a combination thereof capable of forming new contractile tissue in and/or near an infarct zone of a patient's myocardium; and an electrical stimulation device for electrically stimulating the new contractile tissue in and/or near the infarct zone of the patient's myocardium or otherwise damaged or diseased myocardial tissue.

29 Claims, 2 Drawing Sheets

U.S. PATENT DOCUMENTS

| | | | |
|---|---|---|---|
| 5,158,078 A | 10/1992 | Bennett et al. | 128/419 PG |
| 5,205,810 A | 4/1993 | Guiraudon et al. | 600/16 |
| 5,207,218 A * | 5/1993 | Carpentier et al. | 607/36 |
| 5,243,977 A * | 9/1993 | Trabucco et al. | 607/10 |
| 5,251,621 A * | 10/1993 | Collins | 600/17 |
| 5,306,293 A | 4/1994 | Zacouto | 607/17 |
| 5,312,453 A | 5/1994 | Shelton et al. | 607/19 |
| 5,314,430 A | 5/1994 | Bardy | 607/5 |
| 5,354,316 A | 10/1994 | Keimel | 607/15 |
| 5,510,077 A | 4/1996 | Dinh et al. | 264/485 |
| 5,545,186 A | 8/1996 | Olson et al. | 607/14 |
| 5,632,716 A | 5/1997 | Bui et al. | 600/16 |
| 5,658,237 A | 8/1997 | Francischelli | 600/16 |
| 5,697,884 A | 12/1997 | Francischelli et al. | 600/17 |
| 5,807,556 A * | 9/1998 | Mannion et al. | 607/50 |
| 6,151,525 A | 11/2000 | Soykan et al. | 607/50 |
| 6,671,558 B1 * | 12/2003 | Soykan et al. | 607/50 |
| 6,775,574 B1 * | 8/2004 | Soykan et al. | 607/50 |
| 7,031,775 B1 * | 4/2006 | Soykan et al. | 607/50 |
| 2006/0057693 A1 * | 3/2006 | Simon | 435/173.1 |

FOREIGN PATENT DOCUMENTS

| | | |
|---|---|---|
| EP | 0 487429 B1 | 5/1992 |
| EP | 0 547733 A2 | 6/1993 |
| EP | 0 547733 B1 | 6/1993 |
| EP | 0 627237 A1 | 12/1994 |
| WO | WO 93/04724 | 3/1993 |
| WO | WO 94/11506 | 5/1994 |
| WO | WO 94/21237 A | 9/1994 |
| WO | WO 95/05781 | 3/1995 |
| WO | WO 97/09088 | 3/1997 |
| WO | WO 99/66036 | 12/1999 |
| WO | WO 02/20088 A | 3/2002 |

OTHER PUBLICATIONS

Bansal, et al., Calcium-Regulated Secretion of Tissue Plasmnogen Activator and Parathyroil Hormone from Human Parathyroil Cells, J. of Clinical Endocrinology and Metabolism, 74(2), 1992.

Barr, et al., Efficient Catheter-Mediated Gene Transfer into the Heart using Replication-Defective Adenovirus, Gene Therapy, 1(1):51-58, 1994.

Blaese, et al., T Lymphocyte-Directed Gene Therapy for ADA SCID: Initial Trial Results After 4-Years, Science, 270, 1995.

Bordignon, et al., Gene Therapy in Peripheral Blood Lymphocytes and Bone Marrow for ADA Immunodeficient Patients, Science, 270, 1995.

Bouaziz, et al., Vascular Endothelial Cell Responses to Different Electrically Charged Poly (Vinylidene Fluoride) Supports Unfer Static and Oscillating Flow Conditions, Biomaterials, 1996 Elsevier Science Ltd. Great Britain, 18:107 112, 1997.

Bouaziz, et al., Effect of Constant and Modulated Electrical Charges Applied to the Culture Material on PG12 and TXA2 Secretion by Endothelial Cells, Biomaterials 16(9), 1995.

Bugiardini, et al., Relation of Severity of Symptoms to Transient Myocardial Ischemia and Prognosis in Unstable Angina, American College of Cardiology, JAAC 25(3):597-604, 1995.

Chiu, et al., Cellular Cardiomyoplasty: Myocardial Regeneration with Satellite Cell Implantation, Ann. Thoracic Surgery, 60:12-18, 1995.

Chowdhury, Long-Term Improvement of Hypercholesterolemia After Ex Vivo Gene Therapy in LDLR-Deficient Rabbits, Science, 254, 1991.

Dichek, et al., Enhanced In-Vivo Antithrombotic Effects of Endothelial Cells Expressing Recombinant Plasminogen Activators Transduced with Retroviral Vectors, Basic Science Reports, AHA, Inc., 1996.

Dunn, et al., Seeding of Vascular Grafts with Genetically Modified Endothelial Cells, Secretion of Redombinant TPA Results in Decreased Seeded Cell Retention In-Vitro and In-Vivo, Basic Science Reports, AHA, Inc., 1960.

Ekhterae, et al., Retroviral Vector-Mediated Transfer and Expression of Human Tissue Plasminogen Activator Gene in Human Endothelial and Vascular Smooth Muscle Cells, Jobs Research Laboratories, Dept. of Surgery and the Univ of Michigan, Ann arbor, The Society for Vascular Surgery and International Society for Cardiovascular Surgery, North American Chapter, 1995.

Fletcher, et al., Acute Myocardiol Infarction, Pathophysiology of Heart Disease, Chap. 7:113-129.

French, et al., Direct In-Vivo Gene Transfer into Porcine Myocardium Using Replication-Deficient Adenoviral Vectors, Circulation, 90:2414-2424, 1994.

Gal, et al., Direct Myocardial Transfection in two Aminal Models, Laboratory Investigation., 68(1):18-25, 1993.

Gillis, et al., Secretion of Prostacyclin, Tissue Plasminogen Activator and its Inhibitor by Cultured Adult Human Endothellal Cells Grown on Different Matrices, W.B. Saunders Company, Ltd., 1996.

Grossman, et al., Sucessful Ex Vivo Gene Therapy Directed to Liver in a Patient with Famllial Hypoercholesterolaemia, Nature Genetics, 6, 1994.

Innis, et al., Key Concepts for PCR, edds. PCR Strategies, Academic Press, New York, 1995.

Johns, et al., Adr\enovirus-Mediated Expression of a Voltage-Gated Potassium Channel In-Vitro (Rat Cardiac Myocytes) and In-Vivo (Rat Liver), Journal of Clinical Investigation., 96:1152-1158, 1995.

Kao, et al., Cellular Cardiomyoplasty: Myocardial Repair with Cell Implantation, Landes Bioscience, Chap. 5 & 8, 1997.

Klug, et al., DNA Synthesis and Multinycleation in Embryonic Stem Cell-Derived Cardiomyocytes, American Journal of Physiology, 269(6):1913-1921, part 2 of 3 parts.

Koh, et al., Stable Fetal Cardiomyocyte Grafts in the Hearts of Dystrophic Mice and Dogs, Journal of Clinical Investigation, 96:2034-2042, 1995.

Kohn, et al., Engraftment of Gene-Modified Umbilical Card Blood Cells in Neonates with Adenosine Deaminase Deficiency, Nature Medicine, 10, 1995.

Leor, et al., Adenovirus-Mediated Gene Transfer into Infarcted Myocardium: Feasibility, Timing, and Location of Expression, J. of Molecular and Cellular Cardiology, 28(10):2057-2067, 1996.

Levin, et al., Protein Kinase C and the Stimulation of Tissue Plasminogen Activator Release from Human Endothelial Cells, J. of Biolopgical Chemistry by the American Society for Biochemistry and Molecular Biology, Inc., 264(27):16030-16036, 1989.

Li, et al., Cardiomyocyte Transplantation Improves Heart Function, Annals of Thoracic Surgery, 60:654-661, 1996.

Mesri, et al., Expression of Vascular Endothelial Growth Factor from a Defective Herpes Simplex Virus Type 1 Amplicon Vector Induces angiogenesis in mice, Circulation Research, 76:161-167. 1995.

Meyle, et al., Fibroblast Anchorage to Microtextured Surfaces, J. of Biomedical Materials Research, 27:1553-1557, 1993.

Murry, et al., Muscle Differentiation During Repair of Myocardial Necrosis in Rats via Gene Transfer with MyoD, J. Clin. Invest., 98:2209-2217, 1996.

Murry, et al., Sheletal Myoblast Transplantation for Repair of Myocardial Necrosis, J. Clin. Invest. 98:2512-2523, 1996.

Nabel, Recombinant Gene Expression In Vivo within Endothelial Cells of the Arterial Wall, Science, 244, 1989.

Nilius, et al., Activation of a C1-Current by Hypotonic Volume Increase in Human Endothelial Cells, The Rockefeller University Press, 103:787-805, 1994.

Olson, Remington: the Science and Practice of Pharmacy (Table of Contents), Remington's Pharmaceutical Sciences, (standard reference text) vol. II.

Parmacek, et al., The Structure and Regulation of Expression of the Murine Fast Skeletal Troponin C Gene, J. Biological Chemistry, 265(26):15970-15976, 1990.

Parmacek, et al., Identification and Characterization of a Cardiac-Specific Transcriptional Regulatory Element in the Slow/Cardiac Troponin C Gene, Molecular and Cellular Biology, 12(5):1967-1976, 1992.

Pashos, et al., Temporal Changes in the Care and Outcome of Elderly Patients with AMI, JAMA, 270:1832, 1993.

Robinson, et al., Arterial Delivery of Genetically Labelled Skeletal Myoblasts to the Murine Heart: Long-Term Survival and Phenotypic Modification of Implanted Myoblasts, Cell Transplantation, 5:77-91, 1996.

Robinson, et al., Implantation of Skeletal Myoblast-Derived Cells, Cellular Cardiomyoplasty: Myocardial Repair With Cell Implantation, Eds., Chap. 5:81-107.

Ryan, et al., ACC/AHA Guidelines for the Management of Patients with Acute Myocardial Infarction, American College of Cardiology and American Heart Association, Inc., Published by Elsevier Science, Inc., JACC V. 28(5):1328-1348, 1996.

Sambrook, et al., Molecular Cloning, Cold Spring Harbor Laboratory Press, A Laboratory Manual, 1989.

Santell, et al., Cyclic AMP Potentiates Phorbol Ester Stimulation of Tissue Phasminogen Activator Release and Inhibits Secretion of Plasminogen Activator Inhibitor-1 from Human Endothelial Cells, J. of Biological Chemistry, 263(32):16802-16808, Nov. 15, 1988.

Stokes, System and Method for Genetically Treating Cardiac Conduction Disturbances, U.S. Appl. No. 08/682,277, (P3569 CPA) filed Jul. 17, 1996.

Stokes, et al., System and Method for Enhancing Cardiac Signal Sensing by Cardiac Pacemakers Through Genetic Treatment, U.S. Appl. No. 08/682,433, (P3586) filed Jul. 17, 1996.

Symes, Therapeutic Angiogenesis for Coronary Artery and Peripheral Vascular Disease, Angiogenesis in Health and Disease, XIX Annual Meeting of ISHR-American Section, 1997.

Tam, et al., Molecular Cardiomyoplasty: Potential Cardiac Gene Therapy for Chronic Heart Failure, J. Thoracic Cardiovacular Surgery, 109:918-924, 1995.

Taylor, et al., Delivery of Primary Autologous Skeletal Myoblasts into Rabbit Heart by Coronary Infusion: a Potential Approach to Myocardial Repair, Proceedings of the Association of American Physicians, 109(3):245-253, 1997.

Vlay, et al., Innovations in the Management of Ischemic Cardiomyopathy, American Heart Journal, :235, 1994.

von Recum, et al., Macrophage Response to Microtextured Silicone, Blomaterials, 13:1059-1069, 1992.

von Recum, et al., Texturing of Polymer Surfaces at the Cellular Level, Biomaterials, 12:385-389, 1991.

von Recumin, et al., Anchorage to Microtextured Surfaces, J. of Biomedical Materials Research, 27:1553-1557, 1993.

Williams, et al., Introduction of New Genetic Material into Pluripotenthaematopoietic Stem Cells of the Mouse, Nature, 310, 1984.

Y. van den Eijnden-Schrauwen, et al., Studies on the Acute Release of Tissue-Type Plasminogen Activator from Human Endothelial Cells In Vitro and in Rats In Vivo., The American Society of Hematology, Blood, 85(12):3510-3517, 1995.

Yanagisawa, et al., The Human Preproendothelin-1 Gene: Possible Regulation by Endothelial Phosphoinositide Turnover Signaling, J. of Cardiovascular Pharmacology, Raven Press Ltd., N.Y., 13(5):S13-S17, 1989.

* cited by examiner

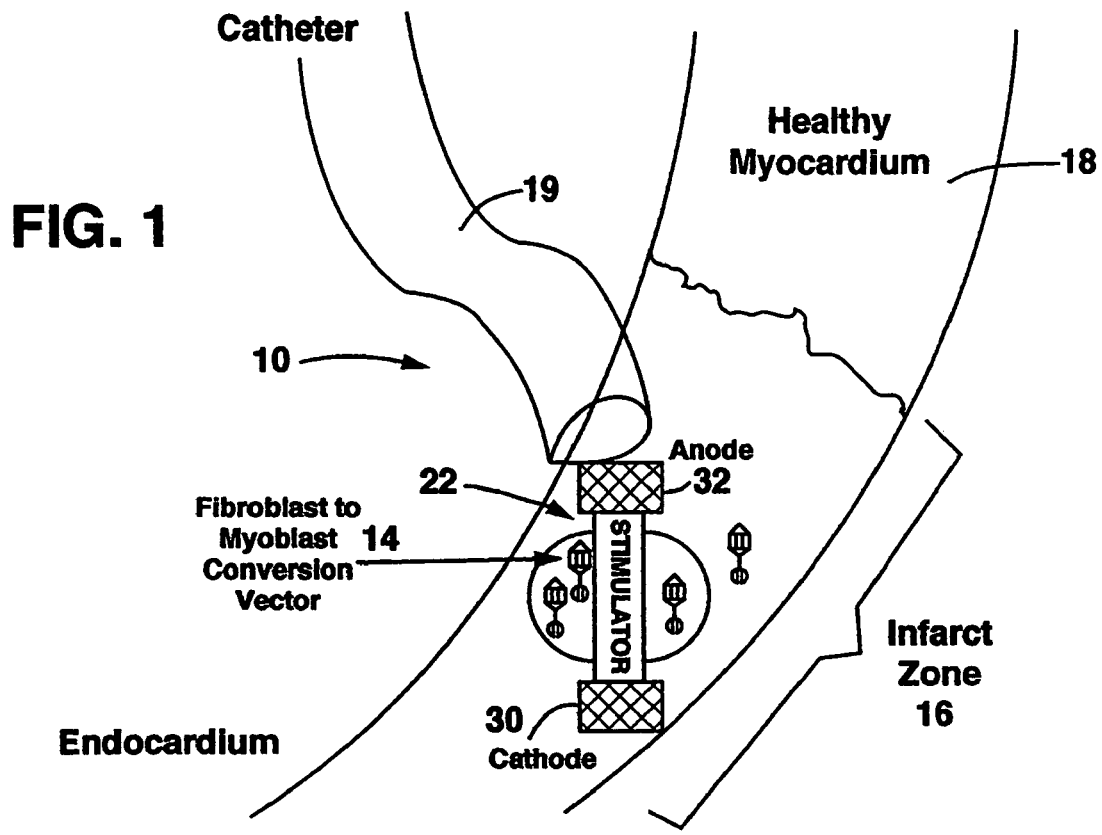
FIG. 1
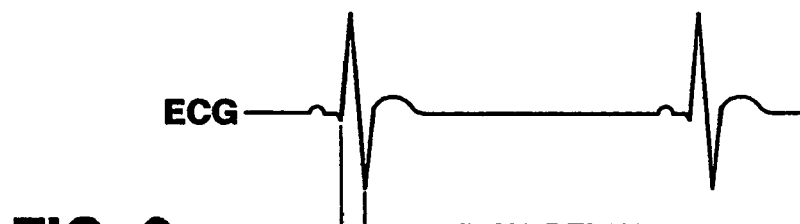
FIG. 2
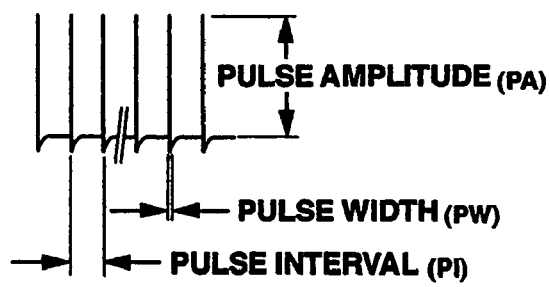

METHOD AND SYSTEM FOR MYOCARDIAL INFARCTION REPAIR

CROSS-REFERENCE TO RELATED TECHNOLOGY

This application is a continuation of patent application Ser. No. 10/692,878 filed Oct. 24, 2003, now U.S. Pat. No. 7,031,775, which is a continuation of patent application Ser. No. 09/706,531 filed Nov. 3, 2000, now U.S. Pat. No. 6,671,558, which is a continuation-in-part of patent application Ser. No. 09/654,185 filed Sep. 1, 2000, now U.S. Pat. No. 6,775,574, which is a continuation of patent application Ser. No. 09/145,743 filed Sep. 2, 1998, now U.S. Pat. No. 6,151,525 which claims priority to provisional application No. 60/064,703 filed on Nov. 7, 1997. This application is related to patent application Ser. No. 10/824,011 filed Apr. 14, 2004 entitled "Method and System for Myocardial Infarction Repair" which is incorporated herein by reference.

FIELD OF THE INVENTION

The present invention relates to methods and implantable systems to reverse damage to heart muscle following myocardial infarction and more generally in and/or near damaged or diseased myocardial tissue. Specifically, this involves the repopulation of the damaged or diseased myocardium with undifferentiated or differentiated contractile cells, which additionally may be formed in situ through the use of genetic engineering techniques, and augmentation with electrical stimulation.

BACKGROUND OF THE INVENTION

Coronary Artery Disease (CAD) affects 1.5 million people in the USA annually. About 10% of these patients die within the first year and about 900,000 suffer from acute myocardial infarction. During CAD, formation of plaques under the endothelial tissue narrows the lumen of the coronary artery and increases its resistance to blood flow, thereby reducing the $O_2$ supply. Injury to the myocardium (i.e., the middle and thickest layer of the heart wall, composed of cardiac muscle) fed by the coronary artery begins to become irreversible within 0.5–1.5 hours and is complete after 6–12 hours, resulting in a condition called acute myocardial infarction (AMI) or simply myocardial infarction (MI).

Myocardial infarction is a condition of irreversible necrosis of heart muscle that results from prolonged ischemia. Damaged or diseased regions of the myocardium are infiltrated with noncontracting scavenger cells and ultimately are replaced with scar tissue. This fibrous scar does not significantly contribute to the contraction of the heart and can, in fact, create electrical abnormalities.

Those who survive AMI have a 4–6 times higher risk of developing heart failure. Current and proposed treatments for those who survive AMI focus on pharmacological approaches and surgical intervention. For example, angioplasty, with and without stents, is a well known technique for reducing stenosis. Most treatments are designed to achieve reperfusion and minimize ventricular damage. However, none of the current or proposed therapies address myocardial necrosis (i.e., degradation and death of the cells of the heart muscle). Because cardiac cells do not divide to repopulate the damaged or diseased region, this region will fill with connective tissue produced by invading fibroblasts. Fibroblasts produce extracellular matrix components of which collagen is the most abundant. Neither the fibroblasts themselves nor the connective tissue they form are contractile. Thus, molecular and cellular cardiomyoplasty research has evolved to directly address myocardial necrosis.

Cellular cardiomyoplasty involves transplanting cells, rather than organs, into the damaged or diseased myocardium with the goal of restoring its contractile function. Research in the area of cellular cardiomyoplasty is reviewed in *Cellular Cardiomyoplasty: Myocardial Repair with Cell Implantation*, ed. Kao and Chiu, Landes Bioscience (1997), particularly Chapters 5 and 8. For example, Koh et al., *J. Clinical Invest.*, 96, 2034–2042 (1995), grafted cells from AT-1 cardiac tumor cell line to canines, but found uncontrolled growth. Robinson et al., *Cell Transplantation*, 5, 77–91 (1996), grafted cells from $C_2C_{12}$ skeletal muscle cell line to mouse ventricles. Although these approaches produced intriguing research studies, cells from established cell lines are typically rejected from the human recipient. Li et al., *Annals of Thoracic Surgery*, 62, 654–661 (1996), delivered fetal cardiomyocytes to adult mouse hearts. They found improved systolic pressures and noticed that the presence of these cells prevented remodeling after the infarction. Although their results showed the efficacy of transplanted cell technology, this approach would not likely be effective in clinical medicine since the syngeneic fetal cardiac tissue will not be available for human patients. Chiu et al., *Ann. Thorac. Surg.*, 60, 12–18 (1995) performed direct injection of cultured skeletal myoblasts to canine ventricles and found that well developed muscle tissue could be seen. This method, however, is highly invasive, which compromises its feasibility on human MI patients.

Molecular cardiomyoplasty has developed because fibroblasts can be genetically manipulated. That is, because fibroblasts, which are not terminally differentiated, arise from the same embryonic cell type as skeletal muscle, their phenotype can be modified, and possibly converted into skeletal muscle satellite cells. This can be done by turning on members of a gene family (myogenic determination genes or "MDGS") specific for skeletal muscle. A genetically engineered adeno-virus carrying the myogenin gene can be delivered to the MI zone by direct injection. The virus penetrates the cell membrane and uses the cell's own machinery to produce the myogenin protein. Introduction of the myogenin protein into a cell turns on the expression of the myogenin gene, which is a skeletal muscle gene, and which, in turn, switches on the other members of the MDGS and can transform the fibroblast into a skeletal myoblast. To achieve this gene cascade in a fibroblast, replication deficient adenovirus carrying the myogenin gene can be used to deliver the exogenous gene into the host cells. Once the virus infects the fibroblast, the myogenin protein produced from the viral genes turns on the endogenous genes, starting the cascade effect, and converting the fibroblast into a myoblast. Without a nuclear envelope, the virus gets degraded, but the cell's own genes maintain the cell's phenotype as a skeletal muscle cell.

This concept has been well-developed in vitro. For example, Tam et al., *J. Thoracic and Cardiovascular Surgery*, 918–924 (1995), used MyoD expressing retrovirus in vitro for fibroblast to myoblast conversion. However, its viability has not been demonstrated in vivo. For example, Klug et al., *J. Amer. Physiol. Society*, 1913–1921 (1995), used SV40 in vivo and succeeded in replicating the nucleus and DNA, but not the cardiomyocytes themselves. Also, Leor et al., *J. Molecular and Cellular Cardiology*, 28, 2057–2067 (1996), reported the in situ generation of new contractile tissue using gene delivery techniques.

Thus, there is a need for an effective system and the method for less invasive delivery of a source of repopulating agents, such as cells or vectors, to the location of the infarct zone of the myocardium and more generally in and/or near damaged or diseased myocardial tissue.

Many of the following lists of patents and nonpatent documents disclose information related to molecular and cellular cardiomyoplasty techniques. Others are directed to background information on myocardial infarction, for example.

TABLE 1a

Patents

| Patent No. | Inventor(s) |
|---|---|
| 4,379,459 | Stein |
| 4,411,268 | Cox |
| 4,476,868 | Thompson |
| 4,556,063 | Thompson et al. |
| 4,821,723 | Baker et al. |
| 5,030,204 | Badger et al. |
| 5,060,660 | Gambale et al. |
| 5,069,680 | Grandjean |
| 5,104,393 | Isner et al. |
| 5,131,388 | Pless |
| 5,144,949 | Olson |

TABLE 1a-continued

Patents

| Patent No. | Inventor(s) |
|---|---|
| 5,158,078 | Bennett et al. |
| 5,205,810 | Guiraudon et al. |
| 5,207,218 | Carpentier et al. |
| 5,312,453 | Shelton et al. |
| 5,314,430 | Bardy |
| 5,354,316 | Keimel |
| 5,510,077 | (Dinh et al.) |
| 5,545,186 | Olson et al. |
| 5,658,237 | Francishelli |
| 5,697,884 | Francishelli et al. |

TABLE 1b

Foreign Patent Documents

| Document No. | Applicant | Publication Date |
|---|---|---|
| WO 93/04724 | Rissman et al. | Mar. 15, 1993 |
| WO 94/11506 | Leiden et al. | May 26, 1994 |
| WO 95/05781 | Mulier et al. | Mar. 02, 1995 |
| WO 97/09088 | Elsberry et al. | Mar. 13, 1997 |

TABLE 1c

Nonpatent Documents

Acsadi et al, The New Biol., 3, 71–81 (1991).
Barr et al., Gene Ther., 1, 51–58 (1994).
Cellular Cardiomyoplasty: Myocardial Repair with Cell Implantation, ed. Kao and Chiu, Landes Bioscience (1997)
Chiu et al., "Cellular Cardiomyoplasty: Myocardiol Regeneration With Satellite Cell Implantation", Ann. Thorac. Surg., 60, 12–18 (1995).
Fletcher et al., "Acute Myocardiol Infarction", Pathophysiology of Heart Disease,
French et al., Circulation, 90, 2414–2424 (1994).
Gal et al., Lab. Invest., 68, 18–25 (1993).
Innis et al. Eds. PCR Strategies, 1995, Academic Press, New York, New York.
Johns, J. Clin. Invest., 96, 1152–1158 (1995).
Klug et al., J. Amer. Physiol. Society, 1913–1921 (1995).
Koh et al., J. Clinical Invest., 96, 2034–2042 (1995).
Leor et al., J. Molecular and Cellular Cardiology, 28, 2057–2067 (1996)
Li et al., Annals of Thoracic Surgery, 60, 654–661 (1996).
Mesri et al., "Expression of Vascular Endothelial Growth Factor From a Defective Herpes Simplex Virus Type 1 Amplicon Vector Induces Angiogenesis in Mice", Department of Medicine, Division of Endocrinology, Diabetes Research Center, Bronx, New York (Received Aug. 19, 1994, accepted Nov. 03, 1994), 1995, American Heart Association.
Molecular Cloning: A Laboratory Manual, 1989 Cold Spring Hrbor Laboratory Press, Cold Spring Harbor, New York.
Murry et al., J. Clin. Invest., 98, 2209–2217 (1196)
Olson, "Remington's Pharmaceutical Sciences", a standard reference text in this field.
Parmacek et al, J. Biol. Chem., 265, 15970–15976 (1990).
Parmacek et al., Mol. Cell. Biol., 12, 1967–1976 (1992).
Robinson et al., Cell Transplantation, 5, 77–91 (1996).
Robinson et al., "Implantation of Skeletal Myoblast-Derived Cells", Cellular Cardiomyoplasty: Myocardiol Repair with Cell Implantation, eds. R. Kao and R. C-J. Chiu, Landes Bioscience (1997).
Sambrook et al., Molecular Cloning: A Laboratory Manual, 1989, Cold Spring Harbor Laboratory Press, Cold Spring Harbor, New York.
Symes, "Therapeutic Angiogenesis for Coronary Artery and Peripheral Vascular Disease", LAD, July 1997 (XIX Annual Meeting of ISHR - American Section.
Tam et al., J. Thoracic and Cardiovascular Surgery, 918–924 (1995).
Taylor et al., "Delivery of Primary Autologous Skeletal Myoblasts into Rabbit Hear by Coronary Infusion: A Potential Approach to Myocardial Repair", Proceedings of the Association of American Physicians, 109, 245–253 (1997).
von Recumin et al., Biomaterials, 12, 385–389, "Texturing of Polymer Surfaces TABLE 1c-continued Nonpatent Documents at the Cellular Level" (1991).
von Recumin et al., Biomaterials, 13, 1059–1069, "Macrophage Response to Microtextured Silicone" (1992).
von Recumin et al., Journal of Biomedical Materials Research, 27, 1553–1557, "Fibroblast Anchorage to Microtextured Surfaces" (1993).
Zibaitis et al., "Cellular Cardiomyoplasty: Biological Basis, Current Hypothesis and Future Perspective", Cellular Cardiomyoplasty: Myocardial Repair with Cell Implantation, eds. R. Kao and R. C-J. Chiu, Landes Bioscience (1997).

All patent and nonpatent documents listed in Table 1 are hereby incorporated by reference herein in their respective entireties. As those of ordinary skill in the art will appreciate upon reading the Summary of the Invention, Detailed Description of Preferred Embodiments, and Claims set forth below, many of the systems, devices, and methods disclosed in these documents may be modified advantageously by using the teachings of the present invention.

SUMMARY OF THE INVENTION

The present invention also provides methods and implantable systems that reverse the damage to necrotic heart muscle following myocardial infarction or in and/or damaged or diseased myocardial tissue. Specifically, this involves combining a method of supplying a source of a repopulating agent with a stimulation device. More specifically, this involves the repopulation of the damaged or diseased myocardium with undifferentiated or differentiated contractile cells and augmentation of the newly formed tissue with electrical stimulation to cause the newly formed tissue to contract in synchrony with the heart to improve the cardiac function.

The present invention comprises (a) a cell repopulation source capable of forming new contractile tissue in and/or near damaged or diseased myocardial tissue. The cell repopulation source may be implanted into a patient's myocardium, preferably where the myocardium has been damaged or diseased, such as where the tissue is after a myocardial infarction. The repopulation source may be delivered directly to the myocardial tissue, such as in an infracted tissue area, by a catheter or more manually by a syringe.

The cell repopulation source may comprise undifferentiated contractile cells, such as skeletal muscle satellite cells, myoblasts, stem or mesenchymal cells and the like, or differentiated cardiac or skeletal cells, such as cardiomyocytes, myotubes and muscle fiber cells, and the like. The implanted cells may be autologous muscle cells, allogenic muscle cells or xenogenic muscle cells, The cell repopulation source may comprise genetic material optionally contained in a delivery vehicle wherein the delivery vehicle may comprise a nucleic acid molecule, such as plasmid DNA, Further, the plasmid DNA may optionally contain at least one gene. The nucleic acid molecule may encode a gene such as a myogenic determination gene. The delivery vehicle may be delivered in liposomes or by any suitable source.

The cell repopulation source may additionally comprise a polymeric matrix, which may further comprise a carrier or the cell repopulation source may be coated on a carrier.

The electrical stimulation device may comprise a muscle stimulator; optionally having two electrodes connected in and/or near the damaged or diseased myocardial tissue and may optionally be a carrier for the cell repopulaton source.

In one mode the electrical stimulation device may provide burst stimulation or pulse stimulation, or combinations thereof.

The repopulation of the damaged or diseased myocardium with undifferentiated or differentiated contractile cells can be carried out using a cellular or a molecular approach. Cellular approaches involve the injection, either directly or via coronary infusion, for example, of undifferentiated or differentiated contractile cells, preferably cultured autologous skeletal cells, into the infarct zone (i.e., the damaged or diseased region of the myocardium). Molecular approaches involve the injection, either directly or via coronary infusion, for example, of nucleic acid, whether in the form of naked, plasmid DNA, optionally incorporated into liposomes or other such delivery vehicle, or a genetically engineered vector into the infarct zone to convert fibroblasts, for example, invading the infarct zone into myoblasts. The genetically engineered vector can include a viral expression vector such as a retrovirus, adenovirus, or an adeno-associated viral vector, for example.

Various embodiments of the present invention provide one or more of the following advantages: restoration of elasticity and contractility to the tissue; increased left ventricular function; reduction in the amount of remodeling (i.e., conversion of elastic and contractile tissue to inelastic and noncontractile tissue); and decreased morbidity and mortality.

In one embodiment, the present invention provides an implantable system comprising: a cell repopulation source comprising genetic material, undifferentiated contractile cells, differentiated contractile cells, or a combination thereof capable of forming new contractile tissue in and/or near an infarct zone of a patient's myocardium and more generally in and/or near damaged or diseased myocardial tissue; and an electrical stimulation device for electrically stimulating the new contractile tissue in and/or near the infarct zone of the patient's myocardium. An infarct zone of a myocardium or damaged or diseased myocardial tissue can be determined by one of skill in the art. Near the infarct zone or damaged or diseased myocardial tissue means sufficiently close that damage to necrotic heart muscle is realized. Typically, this means within about 1 centimeter (cm) of the edge of the infarct zone or damaged or diseased tissue area.

In another embodiment, the present invention provides an implantable system comprising: a cell repopulation source comprising with a suitable cell type, such as skeletal muscle satellite cells, capable of forming new contractile tissue in and/or near an infarct zone or damaged or diseased myocardial tissue area of a patient's myocardium; and an electrical stimulation device for electrically stimulating the new contractile tissue in and/or near the infarct zone of the patient's myocardium, wherein the electrical stimulation device provides burst stimulation.

The present invention also provides a method of repairing the myocardium of a patient, the method comprising: providing an implantable system as described above; implanting the cell repopulation source into and/or near the infarct zone of the myocardium of a patient; allowing sufficient time for the new contractile tissue to form from the cell repopulation source; and electrically stimulating the new contractile tissue. Typically, new contractile tissue forms within about 15 days, although electrical stimulation may not be effective for up to about 14 additional days after the contractile tissue forms.

BRIEF DESCRIPTION OF THE DRAWINGS

FIG. 1 is an illustration of an implantable system according to the present invention.

FIG. 2 is an illustration of a series of pulses a preferred electrical stimulation device provides during ventricular contractions.

DETAILED DESCRIPTION OF THE PREFERRED EMBODIMENTS

Figure 3:
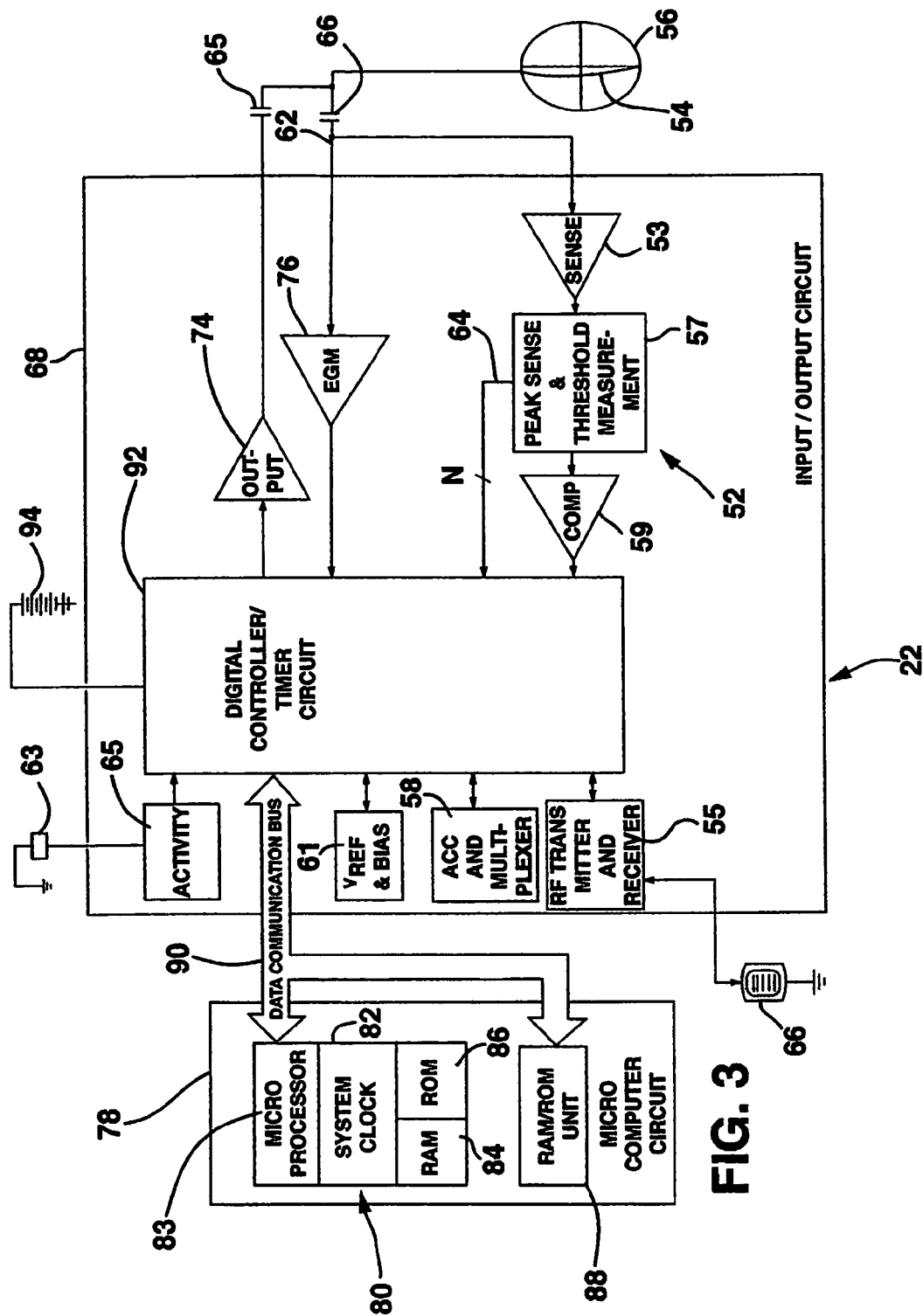
FIG. 3 is a block diagram illustrating various components of an implantable pulse generator (IPG) that can be used according to methods of the present invention.

The present invention comprises (a) a cell repopulation source capable of forming new contractile tissue in and/or near damaged or diseased myocardial tissue. The cell repopulation source may be implanted into a patient's myocardium, preferably wherer the myocardium has been damaged or diseased, such as where the tissue is after a myocardial infarction. The repopulation source may be delivered directly to the myocardial tissue, such as in an infracted tissue area, by a catheter or more manually by a syringe.

The cell repopulation source may comprise undifferentiated or differentiated contractile cells, such as skeletal muscle satellite cells, myoblasts, stem or mesenchymal cells. The implanted cells may be autologous muscle cells, allogenic muscle cells or xenogenic muscle cells.

The cell repopulation source may comprise genetic material optionally contained in a delivery vehicle wherein the delivery vehicle may comprise a nucleic acid molecule, such as plasmid DNA, Further, the plasmid DNA may optionally contains at least one gene. The nucleic acid molecule may encode a gene such as a myogenic determination gene. The delivery vehicle may be delivered in liposomes other any other-suitable source.

The cell repopulation source may additionally comprise a polymeric matrix, which may further comprise a carrier or the cell repopulation source may be coated on a carrier.

The electrical stimulation device may comprise a muscle stimulator; optionally having two electrodes connected in and/or near the damaged or diseased myocardial tissue and may optionally be a carrier for the cell repopulation source. In one mode the electrical stimulation device may provide burst stimulation or pulse stimulation, or combinations thereof.

The present invention also provides methods and implantable systems that reverse the damage to necrotic heart muscle following myocardial infarction by repopulating the damaged or diseased myocardium with undifferentiated or differentiated contractile cells. This repopulation is augmented with electrical stimulation to assure synchrony of the contraction of the newly infused tissue with cardiac contraction.

The repopulation of the damaged or diseased myocardium with undifferentiated or differentiated contractile cells can be carried out using a variety of cellular or molecular approaches. Typically, any of a variety of techniques by which undifferentiated or differentiated contractile cells repopulate the infarct zone of the myocardium can be used. In one specific application, they can involve delivering undifferentiated contractile cells to the infarct zone or transforming cells and growing undifferentiated contractile cells in situ, for example.

Cellular approaches involve the injection, either directly or via coronary infusion, for example, of undifferentiated or differentiated contractile cells, preferably cultured myoblasts (i.e., muscle cells), and more preferably, skeletal or cardiac myoblasts, into the infarct zone (i.e., the damaged or diseased region of the myocardium) of the heart. Preferably, the cells are autologous to reduce and/or eliminate the immune response and tissue rejection. Typically, upon injection, skeletal myoblasts differentiate into cardiac muscle fibers.

Molecular approaches involve the injection, either directly or via coronary infusion, for example, of nucleic acid, whether in the form of naked, plasmid DNA, optionally incorporated into liposomes or similar vehicle, or a genetically engineered vector, into the infarct zone to convert blastular, undifferentiated cells (e.g., fibroblasts or stem cells) invading the infarct zone into myoblasts. The vector can be a viral vector, preferably, an adenoviral vector, that expresses myogenin or MyoD, for example, which are members of the muscle family of genes whose gene products induce fibroblast to myoblast phenotypic conversion.

These regions of repopulated cells provide improved diastolic cardiac function. Significantly, augmenting the repopulated regions with electrical stimulation provides improved systolic as well as diastolic function. As a result, the present invention provides systems and methods that include a cell repopulation source (i.e., a cell repopulating agent) and an electrical stimulation device (i.e. a stimulation source). The cell repopulation source can include undifferentiated contractile cells such as autologous muscle cells, or nucleic acid for conversion of fibroblasts, for example, to myoblasts. The repopulation source can included differentiated cardiac or skeletal cells, such as cardiomyocytes, myotubes and muscle fiber cells, and the like The cell repopulation source can be delivered by direct injection into the myocardium or via the coronary vasculature. Cell repopulation can be carried out using a syringe, or alternatively, a delivery device such as a catheter can be used. The cells or genetic material can be delivered simultaneously with the electrical stimulation device, or they can be delivered separately. Preferably, the electrical stimulation device is the carrier of the cells or genetic material. The electrical stimulation device typically includes an implantable muscle stimulator and electrodes. Significantly, it does not include leads connecting it to any other device.

The cell repopulation source (i.e., cell repopulating agent) can include medicaments, enhancing chemicals, proteins, and the like, for stimulating local angiogenesis, cell contractility, cell growth, and migration, for example. These can include, for example, aFGF (acidic fibroblast growth factor), VEGF (vascular endothelial growth factors), tPA (tissue plasminogen activator), BARK (β-adrenergic receptor kinase), β-blockers, etc. Heparin, or other anticoagulants, such as polyethylene oxide, hirudin, and tissue plasminogen activator, can also be incorporated into the cell repopulation source prior to implantation in an amount effective to prevent or limit thrombosis.

Referring to FIG. 1, an implantable system of the present invention include a delivery device 10 comprising a carrier 22 for undifferentiated contractile cells, and/or differentiated cells, and may separately or additionally include genetic material (i.e., nucleic acid in a variety of forms) or differentiated contractile cells, which is in the form of an electrical stimulator capsule. If desired, other carriers can be designed depending on whether direct injection or coronary infusion is used. As shown in FIG. 1, the carrier 22 is delivered to the infarct zone of a patient's myocardium using a catheter 19. Optionally, no carrier is required for delivery of the cells and/or genetic material, as when the cells and/or genetic material are systemically injected. In FIG. 1, the cell repopulation source is a fibroblast to myoblast conversion vector 14. The cell repopulation source (i.e., cell repopulating agent) is typically released from the carrier 22 by passive diffusion into the infarct zone 16 of a myocardium 18 of a patient's heart.

Undifferentiated and Differentiated Contractile Cells

Cells suitable for implantation in the present invention include a wide variety of undifferentiated contractile cells. Typically, these differentiate to form muscle cells, however, they can be fibroblasts that have been converted to myoblasts ex vivo, or any of a wide variety of immunologically neutral cells that have been programmed to function as undifferentiated contractile cells. Suitable cells for use in the present invention typically include umbilical cells, skeletal muscle satellite cells. Suitable cells for implantation also include differentiated cardiac or skeletal cells, such as cardiomyocytes, myotubes and muscle fiber cells, and the like whether they are autologous, allogeneic or xenogenic, genetically engineered or nonengineered. Mixtures of such cells can also be used. Autologous cells are particularly desirable. The cells are capable of repopulating the infarct zone of the myocardium or capable of establishing health tissue in damaged or diseased myocardial areas.

Skeletal muscle satellite cells are particularly suitable for use in the present invention because they can differentiate to muscle cells that are capable of contracting in response to electrical stimulation. They are also particularly suitable for use in the present invention because they can be obtained from cell cultures derived from the biopsy samples of the same patient. Biopsy samples contain mature skeletal fibers along with reserve cells surrounding the mature fibers. Once placed in culture, reserve cells proliferate and their numbers quickly increase. These newly cultured cells can be injected back into the heart in and/or near the infarct zone. Once in the heart muscle, the skeletal myoblasts fuse to form multinucleated myotubes having contractile characteristics.

Although skeletal muscle cells are capable of contracting, they are different than cardiac cells. The mechanical and electrical characteristics of skeletal muscle are quite different than those of heart muscle. Skeletal muscle satellite cells mechanically contract and relax very rapidly. Therefore, in order to generate sustained contractions, skeletal cells are pulsed fairly rapidly, but this caused quick deprivation of energy reserves and the development of muscle fatigue. However, skeletal muscle can be conditioned to contract at rates similar to or in conjunction with heart muscle.

Skeletal cells also differ from cardiac cells in their electrical characteristics. Each skeletal muscle fiber is stimulated by acetylcholine released from the motor neuron innervating the muscle. However, cardiac cells are interconnected via interclated disks containing channels for the passage of ions between the cytoplasm of the cells. This type of electrical interconnection does not exist between skeletal muscle satellite cells. The use of electrical stimulation circumvents this problem and conditions the cells to contract at rates similar to or in conjunction with heart muscle.

However, any differentiated or undifferentiated cell type that is implanted into the myocardium could benefit by having electrical stimulation to coordinate the contractions in synchrony with normal physiological contractile rhythms.

The undifferentiated and/or differentiated contractile cells can be delivered in combination with a delivery vehicle, such as liposomes or a polymeric matrix, as described in greater detail below.

Once the undifferentiated and/or differentiated cells form contractile tissue, their function can be further enhanced by metabolically altering them, for example, by inhibiting the formation of myostatin. This increases the number of muscle fibers.

Genetic Material

Nucleic acid can be used in place of, or in addition to, the undifferentiated and differentiated contractile cells. The nucleic acid can be in the form of naked, plasmid DNA, which may or may not be incorporated into liposomes or other such vehicles, or vectors incorporating the desired DNA. The nucleic acid is capable of converting noncontracting cells within and/or near the infarct zone or damaged or diseased tissue are of a patient's myocardium to contracting (i.e., contractile) cells. If desired, however, nonundifferentiated contractile cells can be converted to undifferentiated contractile cells using ex vivo genetic engineering techniques and then delivered to the infarct zone.

There are a wide variety of methods that can be used to deliver nucleic acid to nonundifferentiated or differentiated contractile cells. For instance such as fibroblast cells, can be convert their phenotype from connective to contractile. Such methods are well known to one of skill in the art of genetic engineering. For example, the desired nucleic acid can be inserted into an appropriate delivery vehicle, such as, for example, an expression plasmid, cosmid, YAC vector, and the like, to produce a recombinant nucleic acid molecule. There are a number of viruses, live or inactive, including recombinant viruses, that can also be used. A retrovirus can be genetically modified to deliver any of a variety of genes. Adenovirus can also be used to deliver nucleic acid capable of converting nonundifferentiated contractile cells to undifferentiated contractile cells, preferably, muscle cells. A "recombinant nucleic acid molecule," as used herein, is comprised of an isolated nucleotide sequence inserted into a delivery vehicle. Regulatory elements, such as the promoter and polyadenylation signal, are operably linked to the nucleotide sequence as desired.

The nucleic acid molecules, preferably recombinant nucleic acid molecules, can be prepared synthetically or, preferably, from isolated nucleic acid molecules, as described below. A nucleic acid is "isolated" when purified away from other cellular constituents, such as, for example, other cellular nucleic acids or proteins, by standard technique known to those of ordinary skill in the art. The coding region of the nucleic acid molecule can encode a full length gene product or a fragment thereof, or a novel mutated or fusion sequence. The coding sequence can be a sequence endogenous to the target cell, or exogenous to the target cell. The promoter, with which the coding sequence is operably associated, may or may not be one that normally is associated with the coding sequence.

Almost any delivery vehicle can be used for introducing nucleic acids into the cardiovascular system, including, for example, recombinant vectors, such as one based on adenovirus serotype 5, Ad5, as set forth in French, et al., *Circulation*, 90, 2414–2424 (1994). An additional protocol for adenovirus-mediated gene transfer to cardiac cells is set forth in WO 94/11506, Johns, *J. Clin. Invest.*, 96, 1152–1158 (1995), and in Barr, et al., *Gene Ther.*, 1, 51–58 (1994). Other recombinant vectors include, for example, plasmid DNA vectors, such as one derived from pGEM3 or pBR322, as set forth in Acsadi, et al., *The New Biol.*, 3, 71–81, (1991), and Gal, et al., *Lab. Invest.*, 68, 18–25 (1993), cDNA-containing liposomes, artificial viruses, nanoparticles, and the like.

The regulatory elements of the recombinant nucleic acid molecules are capable of directing expression in mammalian cells, specifically human cells. The regulatory elements include a promoter and a polyadenylation signal. In addition, other elements, such as a Kozak region, may also be included in the recombinant nucleic acid molecule. Examples of polyadenylation signals useful to practice the present invention include, but are not limited to, SV40 polyadenylation signals and LTR polyadenylation signals. In particular, the SV40 polyadenylation signal which is in pCEP4 plasmid (Invitrogen, San Diego, Calif.), referred to as the SV40 polyadenylation signal, can be used.

The promoters useful in constructing the recombinant nucleic acid molecules may be constitutive or inducible. A constitutive promoter is expressed under all conditions of cell growth. Exemplary constitutive promoters include the promoters for the following genes: hypoxanthine phosphoribosyl transferase (HPRT), adenosine deaminase, pyruvate kinase, β-actin, human myosin, human hemoglobin, human muscle creatine, and others. In addition, many viral promoters function constitutively in eukaryotic cells, and include, but are not limited to, the early and late promoters of SV40, the Mouse Mammary Tumor Virus (MMTV) promoter, the long terminal repeats (LTRs) of Maloney leukemia virus, Human Immunodeficiency Virus (HIV), Cytomegalovirus (CMV) immediate early promoter, Epstein Barr Virus (EBV), Rous Sarcoma Virus (RSV), and other retroviruses, and the thymidine kinase promoter of herpes simplex virus. Other promoters are known to those of ordinary skill in the art.

Inducible promoters are expressed in the presence of an inducing agent. For example, the metallothionein promoter is induced to promote (increase) transcription in the presence of certain metal ions. Other inducible promoters are known to those of ordinary skill in the art.

Promoters and polyadenylation signals used are preferably functional within the cells of the patient. In order to maximize protein production, regulatory sequences may be selected which are well suited for gene expression in the cardiac cells into which the recombinant nucleic acid molecule is administered. For example, the promoter is preferably a cardiac tissue-specific promoter-enhancer, such as, for example, cardiac isoform troponin C (cTNC) promoter. Parmacek, et al., *J. Biol. Chem.*, 265, 15970–15976 (1990), and Parmacek, et al., *Mol. Cell Biol.*, 12, 1967–1976 (1992). In addition, codons may be selected which are most efficiently transcribed in the cell. One having ordinary skill in the art can produce recombinant nucleic acid molecules which are functional in the cardiac cells.

Genetic material can be introduced into a cell or "contacted" by a cell by, for example, transfection or transduction procedures. Transfection refers to the acquisition by a cell of new genetic material by incorporation of added nucleic acid molecules. Transfection can occur by physical or chemical methods. Many transfection techniques are known to those of ordinary skill in the art including: calcium phosphate DNA co-precipitation; DEAE-dextran DNA transfection; electroporation; naked plasmid adsorption, and cationic liposome-mediated transfection. Transduction refers to the process of transferring nucleic acid into a cell using a DNA or RNA virus. Suitable viral vectors for use as transducing agents include, but are not limited to, retroviral vectors, adeno associated viral vectors, vaccinia viruses, and Semliki Forest virus vectors.

Treatment of cells, or contacting cells, with recombinant nucleic acid molecules can take place in vivo or ex vivo. For ex vivo treatment, cells are isolated from an animal (preferably a human), transformed (i.e., transduced or transfected in vitro) with a delivery vehicle containing a nucleic acid molecule encoding an ion channel protein, and then administered to a recipient.

In one preferred embodiment of in vivo treatment, cells of an animal, preferably a mammal and most preferably a human, are transformed in vivo with a recombinant nucleic acid molecule of the invention. The in vivo treatment typically involves local internal treatment with a recombinant nucleic acid molecule. When performing in vivo administration of the recombinant nucleic acid molecule, the preferred delivery vehicles are based on noncytopathic eukaryotic viruses in which nonessential or complementable genes have been replaced with the nucleic acid sequence of interest. Such noncytopathic viruses include retroviruses, the life cycle of which involves reverse transcription of genomic viral RNA into DNA with subsequent proviral integration into host cellular DNA. Most useful are those retroviruses that are replication-deficient (i.e., capable of directing synthesis of the desired proteins, but incapable of manufacturing an infectious particle). Such genetically altered retroviral expression vectors have general utility for high-efficiency transduction of genes in vivo. Standard protocols for producing replication-deficient retroviruses (including the steps of incorporation of exogenous genetic material into a plasmid, transfection of a packaging cell line with plasmid, production of recombinant retroviruses by the packaging cell line, collection of viral particles from tissue culture media, and infection of the target cells with viral particles) are well known to those of skill in the art.

A preferred virus for contacting cells in certain applications, such as in in vivo applications, is the adeno-associated virus, a double-stranded DNA virus. The adeno-associated virus can be engineered to be replication deficient and is capable of infecting a wide range of cell types and species. It further has advantages such as heat and lipid solvent stability, high transduction frequencies in cells of diverse lineages, including hemopoietic cells, and lack of superinfection inhibition thus allowing multiple series of transductions.

Exemplary nucleic acid that would function as nucleic acid for incorporation into the cells include, but are not limited to, nucleic acid operably encoding a myogenic protein or MyoD protein. The nucleic acid can include an entire gene or a portion of a gene. Exemplary genes include, but are not limited to, the active forms of the myogenin gene or the MyoD gene.

The gene sequence of the nucleic acid delivered by the delivery vehicle (preferably, virus), including nucleic acid encoding proteins, polypeptide or peptide is available from a variety of sources including GenBank (Los Alamos National Laboratories, Los Alamos, N. Mex.), EMBL databases (Heidelberg, Germany), and the University of Wisconsin Biotechnology Center, (Madison, Wis.), published journals, patents and patent publications. All of these sources are resources readily accessible to those of ordinary skill in the art. The gene sequence can be obtained from cells containing the nucleic acid fragment (generally, DNA) when a gene sequence is known. The nucleic acid can be obtained either by restriction endonuclease digestion and isolation of a gene fragment, or by polymerase chain reaction (PCR) using oligonucleotides as primers either to amplify cDNA copies of mRNA from cells expressing the gene of interest or to amplify cDNA copies of a gene from gene expression libraries that are commerically available. Oligonucleotides or shorter DNA fragments can be prepared by known nucleic acid synthesis techniques and from commercial suppliers of custom oligonucleotides such as Amitof Biotech Inc. (Boston, Mass.), or the like. Those skilled in the art will recognize that there are a variety of commercial kits available to obtain cDNA from mRNA (including, but not limited to Stratagene, La Jolla, Calif. and Invitrogen, San Diego, Calif.). Similarly, there are a variety of commercial gene expression libraries available to those skilled in the art including libraries available form Stratagene, and the like. General methods for cloning, polymerase chain reaction and vector assembly are available from Sambrook et al. eds. (*Molecular Cloning: A Laboratory Manual,* 1989 Cold Spring Harbor Laboratory Press, Cold Spring Harbor, N.Y.) and Innis, et al. eds. (*PCR Strategies,* 1995, Academic Press, New York, N.Y.).

Depending on the maximum genome size that a particular viral genome can accommodate or that can be associated with a virus particle, the virus delivering nucleic acid to the cell can include nucleic acid encoding one or more proteins, polypeptides, or peptides. Oligonucleotides can be delivered by virus through the incorporation of oligonucleotides within the virus or associated with the outer surface of the virus using methods well known to one of skill in the art.

Delivery Vehicles and Carriers

In addition to viral vector delivery vehicles, the cell repopulating agent, whether it be genetic material or undifferentiated contractile cells, can include liposomes or a polymeric matrix. These can be coated on or otherwise incorporated into a carrier, which can be the electrical stimulation device.

The cells and/or genetic material can be delivered in liposomes, which are spherical particles in an aqueous medium, formed by a lipid bylayer enclosing an aqueous compartment. Liposomes for delivery of genetic material, for example, are commercially available from Clontech Laboratories UK Ltd., Basingstoke, Hampshire, United Kingdom.

The cells and/or genetic material can be delivered in a polymeric matrix that encapsulates them. The polymeric matrix of this invention can be prepared from a homopolymer, a copolymer (i.e., a polymer of two or more different monomers), or a composition (e.g., a blend) comprising fibrin, for example, with one or more polymers or copolymers, for example. The composition preferably forms a viscoelastic, tear-resistant, biocompatible polymer. The term "viscoelastic" refers to the prescribed "memory" characteristics of a molecule that allow the molecule to respond to stress as if the molecule was a combination of elastic solids and viscous fluids. The term "tear resistant" indicates that when the polymer is exposed to expansion stress, the material does not substantially tear. Tearing refers to the propagation of a nick or cut in the material while under stress. The term "biocompatible" is used herein to refer to a material that does not have toxic or injurious effects on biological systems.

Preferably, the polymeric matrix minimizes or does not exacerbate irritation to the heart wall when the cells and genetic material are in position. The polymeric matrix is preferably nonthrombogenic when applied alone or alternatively when used with anti-thrombogenic agents such as heparin, and the like, or with anti-inflammatory agents such as dexamethasone, and the like. The polymeric matrix can be a biostable or a bioabsorbable polymer depending on the desired rate of release or the desired degree of polymer stability.

The polymeric matrix of this invention can include one or more other synthetic or natural polymers. Suitable polymers include those that are compatible with the cells or genetic material. They can be biostable or biodegradable. These include, but are not limited to, fibrins, collagens, alginates, polyacrylic acids, polylactic acids, polyglycolic acids, celluloses, hyaluronic acids, polyurethanes, silicones, polycarbonates, and a wide variety of others typically disclosed as being useful in implantable medical devices. Preferably, the polymers are hydrophilic.

Preferably, when genetic material, such as a genetically engineered vector, is delivered, it can be incorporated into a crosslinked hydrophilic polyacrylic acid polymer. This would form a high molecular weight hydrogel that could be used as a coating on a carrier, such as the electrical stimulation device. The genetic material is preferably incorporated into the hydrogel just prior to delivery by first swelling the hydrogel.

Preferably, when undifferentiated and/or differentiated contractile cells are delivered, they can be incorporated into a gel of type I collagen. The cells can be initially incorporated into media that includes type I collagen solution. This material can then be poured into a mold containing a carrier, such as the electrical stimulation device. After incubation at a temperature (e.g., 37° C.) and for a time (e.g., 30 minutes) sufficient to crosslink collagen, the coated device can be removed. If needed, the resultant gel/stimulator can be cultured in media for a time (e.g., 14 days) sufficient to allow for cell growth.

Depending on the time of cell integration and proliferation, the polymeric matrix can be in the form of a porous scaffold. This can be made out of polyurethane using a dissolvable salt, as is known in the art of coating stents. The porous polymeric matrix can be coated with extracellular matrix components, such as fibronectin, heparin sulfate, etc., and then seeded with the undifferentiated or differentiated contractile cells which optionally may included added genetic components. The cells can then grow out of the scaffold.

If desired, a fibrin matrix can be used. It can be prepared, for example, by use of a fibrinogen solution and a solution of a fibrinogen-coagulating protein. Fibrin is clotted by contacting fibrinogen with a fibrinogen-coagulating protein such as thrombin. The fibrinogen is preferably used in solution with a concentration of about 10 to about 50 mg/ml with a pH of about 5.89 to about 9.0 and with an ionic strength of about 0.05 to about 0.45. The fibrinogen solution typically contains proteins and enzymes such as albumin, fibronectin, Factor XIII, plasminogen, antiplasmin, and Antithrombin III. The thrombin solution added to make the fibrin is typically at a concentration of up to about 120 NIH units/ml with a preferred concentration of calcium ions between about 0.02 M and 0.2 M. Also preferably, the fibrinogen and thrombin used to make fibrin in the present invention are from the same animal or human species as that in which the cells or genetic material of the present invention will be implanted to avoid cross-species immune reactions.

The resulting fibrin can also be subjected to heat treatment at about 150° C., for about 2 hours to reduce or eliminate antigenicity.

The optional carrier for delivery of the cells and/or genetic material can include the electrical stimulation device, for example, if the cells and/or genetic material are directly injected into the infarct zone of the myocardium. Alternatively, the carrier for delivery of the cells and/or genetic material can include catheters, for example, if the cells and/or genetic material are to be injected via coronary infusion.

The cells and/or genetic material can be associated with the carrier as a coating or a preformed film, for example. If desired, the carrier can be initially coated with an adhesive, such as that available under the trade name CELLTAK BIOCOAT Cell Environments available from Stratech Scientific Ltd., Luton, Bedfordshire, United Kingdom, to enhance adhesion of the polymeric matrix containing the undifferentiated and or differentiated contractile cells and/or genetic material The genetic material and/or undifferentiated and or different tiated contractile cells can also be delivered in a pharmaceutical composition using a catheter, for example. Such pharmaceutical compositions can include, for example, the nucleic acid, in the desired form, and/or cells in a volume of phosphate-buffered saline with 5% sucrose. In other embodiments of the invention, the nucleic acid molecule and/or cells are delivered with suitable pharmaceutical carriers, such as those described in the most recent edition of *Remington's Pharmaceutical Sciences*, A. Osol, a standard reference text in this field.

If genetic material, undifferentiated cells, or differentiated contractile cells are injected separately or in any combination together into a patient separately from the electrical stimulation device, and are in fluid form, a catheter is advanced to the desired site for treatment, e.g., adjacent the site where the electrical stimulation device is to be positioned. The outer distal end of the catheter is open or porous, thus permitting genetic material and/or undifferentiated and/ or differentiated contractile cells in fluid form to be dispensed out of the end. A reservoir connected to the catheter holds a supply of the selected genetic material and/or undifferentiated and/or differentiated contractile cells. Control elements are used for adjustment of the pressure and flow rate, and may be mechanically or electronically controlled. Reference is made to International Publication No. WO 95/05781, for a more detailed description of such a reservoir and catheter combination. This delivery device may or may not include a pump, such as an osmotic pump, for delivering the cell repopulation source.

Electrical Stimulation Devices

The present invention also includes an electrical stimulation device 22. This provides the necessary electrical pulses at the correct time to make the newly formed contractile tissue beat in synchrony with the rest of the heart muscle.

The electrical stimulation device can include a muscle stimulator and separate electrodes. Alternatively, the electrodes can be incorporated into the muscle stimulator. Furthermore, the muscle stimulator should, of course, include a battery for providing electrical current to electrical and electronic circuitry.

The electrical stimulation device can provide burst stimulation, which is typically used for stimulating skeletal muscle cells, or it can provide synchronous single pulse stimulation, which is typically used for stimulating cardiac muscle cells. Alternatively, the electrical stimulation device can provide both burst and synchronous single pulse stimulation. This is particularly desirable if the new contractile tissue formed includes both skeletal and cardiac muscle cells and/or skeletal muscle cells are initially formed and then converted to cardiac muscle cells. A pressure lead, or other means of monitoring a physiological condition such as wall acceleration or intraventricular pressure, can be used to determine when to switch from burst mode to single phase mode of stimulation. If desired, two electrical stimulation devices can be used, one that provides burst stimulation and one that. provides synchronous single pulse stimulation.

Thus, conventional implantable pulse generators (IPGs) may be modified in accordance with the teachings of the present invention to provide an electrical stimulation device 22, although they are typically not desirable to stimulate cardiac muscle tissue that has been infused with cells and/or genetic material because the newly formed contractile tissue typically requires a burst stimulation to create a long-sustained contraction. Preferred systems of the present invention include an implantable stimulator (22 in FIG. 1) and two electrodes (cathode 30 and anode 32 in FIG. 1). Such a stimulator 22 may not include physical leads connecting it to any other device. However, it is possible to provide electrical stimulation from a stimulator implanted in the body at a remote site and connected to the infarct zone using leads. Although this will make the clinical implementation more invasive in nature, it would reduce the complications of the stimulator capsule.

The preferred stimulator 22 shown in FIG. 1 is in the form of a capsule having electrodes 30 and 32 at either end. These electrodes provide electrical contacts for the internal circuitry to sense the passage of the activation wavefront as well as to deliver a series of stimulation pulses necessary to cause the sustained contraction of the newly formed tissue, e.g., skeletal muscle tissue. The stimulator 22 also preferably includes two electronic circuits, a sense amplifier circuit, and a burst generator circuit.

The sense amplifier circuit is associated with a filter to form a sense amplifier. This is used to sense the electrical depolarization waveform as it passes through the infarct zone. While the amplifier increases the gain of this weak signal to the detection circuit, the filter helps to reject the noise signals from nearby muscles and any other electrical devices.

The burst generator circuit provides a series of pulses as shown in FIG. 2 during the ventricular contractions to keep newly formed skeletal muscle tissue contracted. This is necessary to provide a sustained contraction during systole since the skeletal muscle relaxes much faster than cardiac muscle. The stimulator 22 also includes a power supply that provides electrical power to the sense amplifier and the burst generator.

The stimulator 22 can be in the shape of a cylinder, or other appropriate shape suitable for implantation, and of a size sufficiently small for implantation. For example, it can be about 5 mm in diameter and 20 mm in length. Preferred materials include titanium, but other biocompatible materials can also be used. Stimulator 22 may contain a battery or other power source, electronics to detect heart beats and produce burst stimulation, and telemetry circuits for triggering stimulation on demand. Such circuitry can be developed by one of skill in the art, particularly in view of the teachings of U.S. Pat. No. 5,697,884 (Francischelli et al.), U.S. Pat. No. 5,658,237 (Francischelli), U.S. Pat. No. 5,207,218 (Carpentier et al.), U.S. Pat. No. 5,205,810 (Guiraudon et al.), U.S. Pat. No. 5,069,680 (Grandjean), and U.S. Pat. No. 4,411,268 (Cox).

Because a preferred stimulator 22 does not include physical leads connecting it to any other device, stimulator 22 needs to generate its own electrical power. If the heart is assumed to be a 500 Ω load, and 10 pulses are needed at 10 volts for 1 millisecond, then each stimulation will require 0.2 mJ. If the energy conversion has a 20% efficiency, then the 1 mJ of energy will be needed to stimulate the heart at every beat. Since the heart pumps about 50 mL of blood against 120 mm Hg (16 kPa), it does about 800 mJ of work. Therefore, the stimulator harvests about an-eighth of a percent of the mechanical work done by the heart. This can be done by any of a variety of mechanisms that can convert hydrostatic pressure to electrical energy.

Once implanted, typically, the stimulator 22 is preferably not activated for the first few weeks, to allow for contractile tissue growth. It is then turned on with a low synchronization ratio (e.g., 3:1) between the intrinsic heart beats and the device-produced bursts and progressively increased (e.g., to 1:1).

FIG. 3 is a block diagram illustrating various components of a stimulator 22 which is programmable by means of an external programming unit (not shown). One such programmer adaptable for the purposes of the present invention is the commercially available Medtronic Model 9790 programmer. The programmer is a microprocessor device which provides a series of encoded signals to stimulator 22 by means of a programming head which transmits radio frequency encoded signals to IPG 51 according to a telemetry system, such as that described in U.S. Pat. No. 5,312,453 (Wybomy et al.), for example.

Stimulator 22, illustratively shown in FIG. 3, is electrically coupled to the patient's heart 56 by lead 54. Lead 54, which includes two conductors, is coupled to a node 62 in the circuitry of stimulator 22 through input capacitor 60. In the presently disclosed embodiment, an activity sensor 63 provides a sensor output to a processing/amplifying activity circuit 65 of input/output circuit 68. Input/output circuit 68 also contains circuits for interfacing with heart 56, antenna 66, and circuit 74 for application of stimulating pulses to heart 56 to moderate its rate under control of software-implemented algorithms in microcomputer unit 78.

Microcomputer unit 78 comprises on-board circuit 80 which includes system clock 82, microprocessor 83, and on-board RAM 84 and ROM 86. In this illustrative embodiment, off-board circuit 88 comprises a RAM/ROM unit. On-board circuit 80 and off-board circuit 88 are each coupled by a data communication bus 90 to digital controller/timer circuit 92. The electrical components shown in FIG. 3 are powered by an appropriate implantable battery power source 94 in accordance with common practice in the art. For purposes of clarity, the coupling of battery power to the various components of stimulator 22 is not shown in the figures.

Antenna 66 is connected to input/output circuit 68 to permit uplink/downlink telemetry through RF transmitter and receiver unit 55. Unit 55 may correspond to the telemetry and program logic disclosed in U.S. Pat. No. 4,556,063 (Thompson et al.), or to that disclosed in the above-referenced Wybomy et al. patent. Voltage reference ($V_{REF}$) and bias circuit 61 generates a stable voltage reference and bias current for the analog circuits of input/output circuit 68. Analog-to-digital converter (ADC) and multiplexer unit 58 digitizes analog signals and voltages to provide "real-time" telemetry intracardiac signals and battery end-of-life (EOL) replacement functions.

Operating commands for controlling the timing of stimulator 22 are coupled by data bus 90 to digital controller/timer circuit 92, where digital timers and counters establish the overall escape interval of the IPG as well as various refractory, blinking, and other timing windows for controlling the operation of the peripheral components disposed within input/output circuit 68. Digital controller/timer circuit 92 is preferably coupled to sensing circuitry 52, including sense amplifier 53, peak sense and threshold measurement unit 57, and comparator/threshold detector 59.

Sense amplifier 53 amplifies sensed electrocardiac signals and provides an amplified signal to peak sense and threshold measurement circuitry 57. Circuitry 57, in turn, provides an indication of peak sensed voltages and measured sense amplifier threshold voltages on path 64 to digital controller/timer circuit 92. An amplified sense amplifier signal is then provided to comparator/threshold detector 59. Sense amplifier 53 may correspond to that disclosed in U.S. Pat. No. 4,379,459 (Stein).

Circuit 92 is further preferably coupled to electrogram (EGM) amplifier 76 for receiving amplified and processed signals sensed by an electrode disposed on lead 54. The electrogram signal provided by EGM amplifier 76 is employed when the implanted device is being interrogated by an external programmer (not shown) to transmit by uplink telemetry a representation of an analog electrogram of the patient's electrical heart activity. Such functionality is, for example, shown in previously referenced U.S. Pat. No. 4,556,063.

Output pulse generator 74 provides electrical stimuli to the patient's heart 56 or other appropriate location through coupling capacitor 65 in response to a stimulation trigger signal provided by digital controller/timer circuit 92. Output amplifier 74, for example, may correspond generally to the output amplifier disclosed in U.S. Pat. No. 4,476,868 (Thompson).

It is understood that FIG. 3 is an illustration of an exemplary type of device which may find application in the present invention, or which can be modified for use in the present invention by one of skill in the art, and is not intended to limit the scope of the present invention.

Delivery Methods and Devices

The undifferentiated and/or differentiated contractile cells and/or genetic material described above can be delivered into the infarct zone of the myocardium or to damaged or diseased myocardial tissue using a variety of methods. Preferably, the undifferentiated and/or differentiated contractile cells and/or genetic material are directly injected into the desired region.

For direct injection, a small bolus of selected genetic material and/or undifferentiated or differentiated contractile cells can be loaded into a micro-syringe, e.g., a 100 µL Hamilton syringe, and applied directly from the outside of the heart.

Preferably, however, the method of the present invention uses a catheter for direct injection of both the electrical stimulation device and the cell repopulation source. For example, a catheter can be introduced from the femoral artery and steered into the left ventricle, which can be confirmed by fluoroscopy. Alternatively, the catheter can be steered into the right ventricle.

The catheter includes an elongated catheter body, suitably an insulative outer sheath which may be made of polyurethane, polytetrafluoroethylene, silicone, or any other acceptable biocompatible polymer, and a standard lumen extending therethrough for the length thereof, which communicates through to a hollow needle element. The catheter may be guided to the indicated location by being passed down a steerable or guidable catheter having an accommodating lumen, for example as disclosed in U.S. Pat. No. 5,030,204 (Badger et al.); or by means of a fixed configuration guide catheter such as illustrated in U.S. Pat. No. 5,104,393 (Isner et al.). Alternately, the catheter may be advanced to the desired location within the heart by means of a deflectable stylet, as disclosed in PCT Patent Application WO 93/04724, published Mar. 18, 1993, or by a deflectable guide wire as disclosed in U.S. Pat. No. 5,060,660 (Gambale et al.). In yet another embodiment, the needle element may be ordinarily retracted within a sheath at the time of guiding the catheter into the patient's heart.

Once in the left (or right) ventricle, the tip of the catheter can be moved around the left ventricular wall as a prove to measure the electrogram and to determine the location and extent of the infarct zone. This is a procedure known to one of skill in the art. Once the infarct zone is identified, the steering guide will be pulled out leaving the sheath at the site of infarction. The cell repopulation source and/or electrical stimulation device can then be sent down the lumen of the catheter and pushed into the myocardium. The catheter can then be retracted from the patient.

The electrical stimulation device can include a variety of mechanisms for holding it in place in the myocardium. For example, it can include extendable hooks or talons. Alternatively, the tissue contacting portion of the device can be treated to achieve a microsurface texture (as disclosed by Andreas F. von Recumin in: *Biomaterials,* 12, 385–389, "Texturing of Polymer Surfaces at the Cellular Level" (1991); *Biomaterials,* 13, 1059–1069, "Macrophage Response to Microtextured Silicone" (1992); and *Journal of Biomedical Materials Research,* 27, 1553–1557, "Fibroblast Anchorage to Microtextured Surfaces" (1993)). In an alternative embodiment, the stimulator can be in the form of a screw that is driven into the muscle wall by turning.

EXAMPLES

The following examples are intended for illustration purposes only.

Example 1

Transformation of Fibroblasts In Situ and Electrical Stimulation

Adenovirus expressing myogenin (Myogen adenovirus/cDNA, which can be produced according to the method described by Murry et al., *J. Clin. Invest.,* 98, 2209–2217 (1196)) was injected directly to the myocardium using a 100 microliter syringe. $10^9$ pfu (pfu-plaque forming units-one pfu is approximately 50 adenovirus particles) were diluted with saline to form a 100 microliter solution. This solution was kept on dry ice until the injection, and delivered in four equal amounts to the perimeter of the infarct zone, 90 degrees apart.

A histopathological assessment of the treated tissue was done to assess the extent of fibroblast transformation. Tissue was processed for histology and stained with H&E and Masson's Trichrome according to standard methods.

Immunohistochemical staining was also done to determine whether there was myogenin expression in the treated tissue. Eight μm frozen sections were cut from the tissue, fixed, and incubated with a rabbit polyclonal IgG that was raised against rat myogenin (Santa Cruz Biotechnology, Inc. Cat. No. sc-576). The samples were rinsed, incubated with a labeled secondary antibody and visualized by epiflourescent microscopy.

Delivery of adenovirus expressing myogenin to infarcted tissue in vivo resulted in the appearance of multiple small patches of skeletal myoblasts. These isolated muscle cells had peripheral nuclei, indicating that they were more likely to be skeletal muscle cells than cardiac muscle cells as analyzed histologically. Typically, genetically converted cells represented a more immature form of skeletal muscle than the myotubes seen in myoblast injected tissues (i.e., prior to fusion). No myogenin immunoreactivity was present in these cells at the time of sacrifice. Therefore, it was concluded that the myogenin created by the adenovirus was no longer present at the time of the tissue harvest (as was expected at two weeks after delivery of the virus, since adenovirus expression does not pursue for more than one week to 10 days in vivo).

In cryoablated, adenovirus beta-galactosidase injected hearts, only fibroblasts and lymphocytic infiltrate along with small capillaries were detected within the infarct, similar to the results obtained with animals receiving cryoablation, but no viral injections (control). Thefore, in this control group, no muscle cells or positive staining for myogenin was detected. This comprised the placebo group of the molecular arm of the study.

Example 2

Injection of Contractile Cells and Electrical Stimulation in Canines

Growth and Passage Information for Skeletal Myoblast Cells

1. Growth Medium Formulation:
    81.6% M199 (Sigma, M4530)
    7.4% MEM (Sigma, M-4655)
    10% Fetal Bovine Serum (Hyclone, Cat.#A-1115-L)
    1× (1%) Penicillin/Streptomycin (Final Conc. 100,000 U/L Pen./10 mg/L Strep., Sigma, P-0781).
2. Cell Passage Information:
    A. Seeding densities of $1\times10^4$ cells/cm$^2$ will yield an 80% confluent monolayer in approximately 96 hours.
    B. Split ratios of 1:4–1:6 will yield a confluent monolayer within 96 hours.
    C. Do not allow the cells to become confluent. Cell to cell contact will cause the cells to differentiate into myotubes.
3. Passage Information:

| Flask Size | ml of HBSS | ml of Trypsin Solution | ml of Media/Flask |
| --- | --- | --- | --- |
| T-25 | 3 | 3 | 10 |
| T-75 | 5 | 5 | 20–35 |
| T-150 | 10–15 | 10–15 | 40–60 |
| T-225 | 15–25 | 15–25 | 60–125 |

A. Remove culture medium from T-flask.
B. Add back the appropriate amount of Hank's Balanced Salt Solution (HBSS).
C. Incubate for approximately 5 minutes at room temperature.

D. Remove HBSS and replace with the Trypsin solution.
E. Incubate for a maximum of 5 minutes at 37° C. in a 5% $CO_2$ incubator. Cells will detach from the cell culture substrate prior to 5 minutes.
F. Do not trypsinize for a longer period than necessary. The cells will be shocked if allowed to remain in the trypsin for longer than 5 minutes.
G. Gently agitate flask to remove cells.
H. Add back at least an equal volume of growth medium to neutralize the trypsin.
I. Remove a sample for cell count.
J. Centrifuge the cells at 1000 RPM for 10 minutes.
K. Count cells and calculate cell numbers.
L. Resuspend in cell culture medium and seed into appropriate flasks.
M. To maintain a healthy culture, change medium every 2–3 days.

4. Cell Count:
A. Dilute cells into the appropriate diluent (Trypan Blue or HBSS). No dilution or 1:2 dilution works well for a confluent T-flask.
B. Count cells using a hemocytometer. The most accurate range for the hemocytometer is between 20–50 cells/square.
C. Calculation:
   Cells counted (divided by) squares counted (multiplied by) dilution factor (multiplied by) $1 \times 10^4$=cells/ml in the original cell suspension.

Enzymatic Myoblast Isolation

Skeletal muscle, unlike cardiac muscle, retains the ability to repair itself if damaged or diseased. The reason for this is the presence of undifferentiated myoblasts (also referred to as satellite cells) located in the mature muscle.

Mature muscle myotubes can't be grown in culture, because in the process of differentiating from myoblasts to myotubes the cells loose the ability to proliferate. In order to conduct in vitro research on skeletal muscle myotubes it is first necessary to first isolate the muscle myoblasts. The following procedure is for isolating primary muscle myoblasts from skeletal muscle biopsies and sub-culturing the resulting cells.

1. Materials:
A. Isolation Medium: 80.6% M199 (Sigma, M-4530), 7.4% MEM (Sigma, M-4655), 10% Fetal Bovine Serum (Hyclone, Cat.#A-1115-L), 2× (2%) Penicillin/Streptomycin (Final Conc. 200,000 U/L Pen./20 mg/L Strep., Sigma, P-0781).
B. Myoblast Growth Medium: 81.6% M199 (Sigma, M-4530), 7.4% MEM (Sigma, M-4655), 10% Fetal Bovine Serum (Hyclone, Cat.#A-1115-L), 1× (1%) Penicillin/Streptomycin (Final Conc. 100,000 U/L Pen./10 mg/L Strep., Sigma, P-0781).
C. Wash Solution: M199, 2× Penicillin/Streptomycin.
D. Collagenase (Crude: Type IA, Sigma, C-2674).
E. Hyaluronidase (Type I-S, Sigma, H-3506).
F. Protease, from Streptomyces griseus, (Sigma, P-8811).
G. Hank's Balanced Salt Solution (HBSS), $Ca^{2+}$ and $Mg^{2+}$ free (Sigma, H-6648).
H. 70% EtOH (sterile filtered).
I. Percoll (Sigma, P-4937).
J. 0.5 g/L Trypsin Solution (Sigma, T-3924).
K. 15 ml and 50 ml Sterile Centrifuge Tubes.
L. 100 mm Sterile Petri Dish.
M. Sterile Scissors and Sterile Forceps (Fine Scientific Tools).
N. 5 ml, 10 ml, 25 ml Sterile Pipettes (Falcon).
O. BIOCOAT Laminin Cellware (25 $cm^2$ and 75 $cm^2$ flasks, Becton Dickinson, Cat. No(s). 40533, 40522)
P. T-75 Tissue Culture Flasks, 0.22 μm vented cap (Corning).
Q. Filter, 0.22 μm and 0.45 μm, cellulose acetate (Corning).
R. Polycarbonate Centrifuge Tubes.
S. Beckman Centrifuge, GS-6.
T. Incubator Shaker.

2. Method:
All steps of this procedure should be performed aseptically.
A. Prepare Isolation Medium:
   Add approximately 30 ml to a 50 ml sterile centrifuge tube (10 gm biopsy or less).
   Add approximately 50 ml to a 125 ml sterile media bottle (up to 25 gm biopsy).
B. Place the Isolation Medium on ice or ice packs to keep cold (approximately 4° C.).
C. Prepare the enzyme solution, the same day it will be used, by adding 1.0 gm collagenase and 0.2 gm hyaluronidase to 100 ml of M199 (100 ml of enzyme/disbursing solution is enough to digest 40–50 gm of skeletal muscle).
D. Filter sterilize the enzyme solution first through a 0.45 μm filter and then a 0.22 μm filter and keep at 4° C. until ready to use.
E. Prepare the disbursing solution, the same day it will be used, by adding 1 gm of the protease to 100 ml of M199.
F. Filter sterilize through a 0.22 μm filter and keep at 4° C. until ready to use.
G. Under semi-sterile conditions remove the skeletal muscle biopsy, preferably from the belly of the muscle, and place it into the isolation medium.
H. Seal the container and store at approximately 4° C. until ready to mince.
I. Remove the tissue and place into a sterile petri dish.
J. Trim off any connective tissue and measure the final weight.
K. Rinse the tissue with sterile 70% EtOH for 30 seconds.
L. Aspirate the EtOH and rinse the tissue 2× with HBSS.
M. Finely mince the biopsy using scissors and tweezers.
N. Transfer the minced biopsy into 50 ml sterile centrifuge tubes. No more than 20 gm/tube to allow for effective enzymatic digestion.
O. Rinse the tissue by adding approximately 25 ml/tube of HBSS, mix, and pellet the tissue by centrifuging at 2000 RPM (allow the centrifuge to reach 2000 RPM and turn off).
P. Decant off the HBSS and repeat the rinse and centrifuge an additional two more times.
Q. Add enzyme solution to the tubes (approximately 25 ml/15 gm—20 gm original biopsy).
R. Incubate tubes in the incubator shaker for 20 minutes (Set Point—37° C., 300 RPM).
S. Centrifuge at 2000 RPM for 5 minutes and discard the supernatant.
T. Add disbursing solution to the tubes (approximately 25 ml/15 gm—20 gm original biopsy).
U. Incubate tubes in the incubator shaker for 15 minutes (Set Point—37° C., 300 RPM).
V. Centrifuge at 2000 RPM for 5 minutes.
W. Harvest the supernatant, inactivate the enzyme by adding FBS to a final concentration of 10%, and store at 4° C.
X. Add disbursing solution to the tubes for a second enzymatic digestion (approximately 25 ml/15 gm—20 gm original biopsy).

Y. Incubate tubes in the incubator shaker for 15 minutes (Set Point—37° C., 300 RPM).
Z. Centrifuge at 2000 RPM for 5 minutes.
AA. Harvest the supernatant and inactivate the enzyme by adding FBS to a final concentration of 10%.
BB. Centrifuge the cell slurry from the disbursing digestion steps (refer to W and AA) at 2400 RPM for 10 minutes.
CC. Remove and discard the supernatant.
DD. Resuspend the cell pellets in a minimal volume of Wash Solution.
EE. Combine the pellets in a 50 ml centrifuge tube, bring the volume up to 40 ml using Wash Solution.
FF. Centrifuge at 2400 RPM for 10 minutes.
GG. Remove the supernatant and repeat the cell wash two more times.
HH. On the final rinse resuspend the pellet in 2 ml of MEM. If the initial biopsy was close to or greater than 25 gm resuspend into 4 ml of MEM.
II. Prepare 20% Percoll and 60% Percoll in MEM.
JJ. Make the density gradient by layering 10 ml of 20% Percoll/MEM over 5 ml of 60% Percoll/MEM (refer to FIG. 1).
KK. Add 2 ml of the cell suspension on the top of the 20% Percoll band.
LL. Use a scale to prepare a second tube as a counter balance for centrifugation.
MM. Centrifuge at 11947 RPM (15000×g) for 5 minutes at 8° C. (adjust acceleration to 5 and brake to 0).
NN. Isolate the band of cells that develops between the 20% and 60% Percoll layers. This band contains the myoblast cells.
OO. Determine the volume of the band and dilute it with 5 volumes of growthmedium.
Note: If the Percoll isn't diluted with enough growth medium it will be very difficult to pellet the myoblasts out of solution.
PP. Centrifuige at 3000 RPM for 10 minutes.
QQ. Remove the supernatant and resuspend the pellet in growth medium.
RR. Count the cells in suspension.
SS. Plate out the cells in the BIOCOAT Laminin coated T-flasks at approximately $1 \times 10^4$ cells/cm$^2$. The first plating should be done on a laminin coated surface to aid in cell attachment.
TT. Culture the cells to 60%–80% confluence. If the cells are allowed to become confluent they will terminally differentiate into myotubes.
UU. Trypsinization Procedure:
Wash the monolayer with HBSS
Add trypsin (0.5 g/l trypsin)

| T-Flask | ml of HBSS | ml of Trypsin |
|---------|------------|---------------|
| T-25    | 3          | 3             |
| T-75    | 5          | 5             |
| T-150   | 10         | 10            |

Incubate at 37° C. for no more than 5 minutes
Neutralize the trypsin with serum containing medium
Remove the cells
Centrifuge at 800 rpm for 10 minutes
Re-suspend in Myoblast Growth Medium
Seed cell culture treated T-flasks at approximately $1 \times 10^4$ cells/cm$^2$.

Split ratio's of 1:4 to 1:6 work well for a 60–80% confluent culture.

Development of Canine Infarct Model and Cell Injection

Myocardial infarction was created in the canine heart by cryoablating a round region of the left ventricular free wall, approximately 3.5 cm in diameter. This was achieved by first performing a left thoracotomy at the fourth or fifth intercostal space to have access to the canine's heart. The heart was re-positioned to have access to the LV free wall. A region relatively free of coronary vasculature was identified for cryoablation.

The myocardium was infarcted by applying a custom cryoablation instrument with a 3.5 cm diameter metal plate to the epicardial surface for up to 10 minutes. Since the probe was cooled with liquid nitrogen, its temperature was as cold as minus 180° C. before it was applied to the surface of the heart. Because the volume of blood flowing within the left ventricle of the dog is enough to warm the endocardial surface, a true transmural ablation could not be achieved. Nevertheless, 13.5 grams of the LV free wall, constituting 15 percent of the LV free wall mass, was ablated. This is a typical size of infarct for a human patient as well.

For one dog, $1.79 \times 10^8$ (one hundred and seventy nine million) myoblasts were obtained within 11 days from 2.5 grams of skeletal muscle biopsy. These cells were reinjected into the canine myocardium at ten locations around the ablation site, using a syringe with a 22 gauge needle and injecting 0.5 mL per site ($1.79 \times 10^8$ cells/5 mL of saline).

In Vivo Electrical Stimulation

Two weeks after the introduction of the MI, the chest was opened again, and the animal was instrumented as before. In addition, an electrode was attached to the ventricular apex for unipolar VVI pacing. Two more electrodes were attached to either sides of the infarcted area to stimulate the cellular cardiomyoplasty region.

It was noticed at this time that the animal's LV pressures and stroke volume were not improved significantly. As a matter of fact, peak systolic pressures were only slightly over 80 mm Hg, and the stroke volume was again around 22 mL when the animal was VVI paced. This suggests that cell placement alone did not appreciably improve the systolic function.

When the skeletal muscle stimulator was turned on, systolic pressures reached 100 mmHg, and stroke volumes increased to 40 mL. Due to synchronization problems between the ventricular pacer and the skeletal muscle stimulator, a stable trace could not be obtained during the study. Nevertheless, this experiment gave an indication that the presence of the skeletal cells alone might not be enough to improve the systolic function, and that there might be a need for skeletal muscle stimulation to improve the cardiac function in conjunction with cellular cardiomyoplasty.

Changes in the wall motion in the region of treatment were also observed with the application of skeletal muscle stimulation. With traditional ventricular pacing only (upper trace), the length of the infarct zone shortened by only 0.5 mm. However, when skeletal muscle stimulation was applied in addition to ventricular pacing, the shortening about 1.0 mm, indicating that wall motion, or contractility, was increased by electrically stimulating the skeletal cardiomyoplasty region.

Histopathological Methods and Results

In order to assure that the transplanted skeletal cells were present at the end of the two week period, preserved tissue sections were analysed with immuno-histochemistry using an anti-myosin antibody (skeletal, fast, MY-32). Positive (green) staining at two different regions of the ablated site indicated the presence of the injected skeletal muscle cells in the ablated region of myocardium, two weeks after their introduction. This immuno-staining study provided definitive evidence for the presence of skeletal muscle cells in the myocardium. The immuno-histochemistry staining protocol used is described as follows:

Immuno-Histological Staining Protocol

Materials:
Monoclonal Anti-Skeletal Myosin (Fast), clone MY-32, Sigma, Cat.No. M-4276.
Polyclonal Rabbit Anti-Connexin-43, Zymed, Cat.No. 71-0700.
Goat Anti-Mouse IgG-FITC, Sigma, Cat.No. F-O257.
Goat Anti-Rabbit IgG (Whole Molecule)-TRITC, Sigma, Cat.No. T-6778.
PBS, Sigma, Cat.No. 1000-3.
Goat Serum, Sigma.
Acetone, Sigma, Cat.No. A-4206.
Mounting Medium, Sigma Cat.No. 1000-4.
Microscope, Nikon, Labophot-2.
Samples:
Skeletal Muscle (Control)
Posterior Lesion
Mid Lesion
Anterior Lesion
J(L) Ventricular Free Wall (Control)

Methods:
A. Clean glass slides with 95% EtOH and treat with poly-Lysine or buy pre-treated slides.
B. Obtain tissue samples and freeze onto cryostat chucks.
C. Cut 8 μm thick cryostat sections of the frozen tissue block, place on treated glass slides, and store at $\leq -70°$ C.
D. Allow tissue sections to come to room temperature prior to initiating staining (approximately 15–30 minutes).
E. Fix samples in cold Acetone ($\leq -10°$ C.) for 10 minutes at 4° C.
F. Wash sample with PBS three times (care must be taken to avoid washing the sample off of the slide).
G. Block samples with 10% Goat Serum/PBS for 20 minutes at room temperature, using a humidified chamber.
H. Dilute the first primary antibody, Connexin-43, 1:100 in PBS containing 10% goat serum. Dilute enough antibody to cover the samples (approximately 150 μl), add to the tissue sections, and incubate in a humidified chamber for 1 hour at room temperature.
I. Wash sample in 10% Goat Serum/PBS three times (5 minutes/wash).
J. Dilute the second primary antibody, My-32, 1:200 in PBS containing 10% goat serum. Dilute enough antibody to cover the samples (approximately 150 μl), add to the tissue sections, and incubate in a humidified chamber for 1 hour at room temperature
K. Wash samples in 10% Goat Serum/PBS three times (5 minutes/wash).
L. Dilute the secondary antibodies, mix the antibody solutions, and add to the tissue sections.
Anti-Rabbit IgG (Whole Molecule)-TRITC, 1:50 in PBS.
Anti-Mouse IgG-FITC, 1:100 in PBS.
M. Incubate in a dark, humidified chamber, for 45 minutes at room temperature.
N. Wash samples in PBS three times (5 minutes/wash).
O. Add mounting medium and a coverslip.
P. Read on the microscope using the FITC filter, the TRITC filter, and the UV light source.
Q. Store samples in a dark chamber at $\leq 4°$ C.

The complete disclosures of the patents, patent applications, and publications listed herein are incorporated by reference, as if each were individually incorporated by reference. The above examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. An implantable system comprising:
(a) a cell repopulation source of stem cells for a patient's myocardium; and
(b) an electrical stimulation device for electrically stimulating the new contractile tissue in and/or near the infarct zone of the patient's myocardium, wherein the electrical stimulation device provides burst stimulation.

2. A method of repairing the myocardium of a patient, the method comprising:
(a) providing an implantable system comprising:
(i) a cell repopulation source comprising genetic material, stem cells, or a combination thereof, capable of forming new contractile tissue in and/or near an infarct zone of a patient's myocardium; and
(ii) an electrical stimulation device for electrically stimulating the new contractile tissue in and/or near the damaaed or diseased myocardial tissue;
(b) implanting the cell repopulation source into and/or near damaged or diseased myocardial tissue of a patient;
(c) allowing sufficient time for new contractile tissue to form from the cell repopulation source; and
(d) electrically stimulating the new contractile tissue.

3. The method of claim 2 wherein the electrical stimulation device comprises an electrical stimulation device with electrodes; wherein the electrodes are implanted to stimulate said new contractile tissue.

4. The method of claim 2 wherein the cell repopulation source is delivered through a catheter.

5. The method of claim 2 wherein the cell repopulation source comprises autologous cells.

6. The method of claim 2 wherein the cell repopulation source comprises mesenchymal stem cells.

7. The method of claim 2 wherein the step of implanting the cell repopulation source into and/or near damaged or diseased myocardial tissue the cells are implanted into the infarct zone of the myocardiumof a patient.

8. The method of claim 2 wherein the electrical stimulation device is implantable and is in the form of a capsule having electrodes incorporated therein.

9. The method of claim 8 wherein the electrical stimulation device is a carrier for the cell repopulation source.

10. An implantable system comprising:
(a) a cell repopulation source of stem cells capable of forming new contractile tissue in and/or near damaged or diseased myocardial tissue; and
(b) an electrical stimulation device for electrically stimulating the new contractile tissue formed in the myocardial tissue.

11. The implantable system of claim 1 wherein the cell repopulation source of stem cells is a mesenchymal stem cell.

12. The implantable system of claim 10 wherein the cell repopulation source of stem cells comprise autologous cells.

13. The implantable system of claim 10 wherein the cell repopulation source further comprises a polymeric matrix.

14. The implantable system of claim 10 wherein the electrical stimulation device provides burst stimulation.

15. The implantable system of claim 10 wherein the electrical stimulation device provides pulse stimulation.

16. The implantable system of claim 10 wherein the cell repopulation source of stem cells comprise allogenic cells.

17. The implantable system of claim 10 wherein the cell repopulation source is associated with a carrier.

18. The implantable system of claim 17 wherein the cell repopulation source is coated on a carrier.

19. The implantable system of claim 1 wherein the electrical stimulation device further comprises an electrical stimulation device having two electrodes connected thereto.

20. The implantable system of claim 19 wherein the is electrical stimulation device implantable and is in the form of a capsule having electrodes incorporated therein.

21. The implantable system of claim 20 wherein the electrical stimulation device is a carrier for the cell repopulation source.

22. The implantable system of claim 10 wherein the cell repopulation source comprises genetic material.

23. The implantable system of claim 22 wherein the genetic material comprises plasmid DNA.

24. The implantable system of claim 22 wherein the genetic material comprises a delivery vehicle comprising a nucleic acid molecule.

25. The implantable system of claim 24 wherein the nucleic acid molecule encodes a myogenic determination gene.

26. The implantable system of claim 24 wherein the delivery vehicle comprises a viral expression vector.

27. The implantable system of claim 24 wherein the delivery vehicle comprises liposomes.

28. The implantable system of claim 24 wherein the nucleic acid molecule encodes VEGF.

29. The implantable system of claim 24 wherein the nucleic acid molecule encodes aFGF.

* * * * *

UNITED STATES PATENT AND TRADEMARK OFFICE
CERTIFICATE OF CORRECTION

PATENT NO. : 7,155,288 B2 Page 1 of 1
APPLICATION NO. : 11/300176
DATED : December 26, 2006
INVENTOR(S) : Orhan Soykan and Maura G. Donovan It is certified that error appears in the above-identified patent and that said Letters Patent is hereby corrected as shown below:

Patent Col. 26, Line 34:   ....the damaaed or...   should read   ....the damaged or...

Signed and Sealed this

First Day of January, 2008

JON W. DUDAS
*Director of the United States Patent and Trademark Office*